US012616686B2

(12) United States Patent
Gao et al.

(10) Patent No.: US 12,616,686 B2
(45) Date of Patent: May 5, 2026

(54) DONEPEZIL ORAL FILMS

(71) Applicant: Xiamen LP Pharmaceutical Co., Ltd., Xiamen (CN)

(72) Inventors: Zhoue Gao, Xiamen (CN); Jing Yin, Xiamen (CN); Zhichao Lin, Xiamen (CN); Yanyan Wang, Xiamen (CN); Avinash Singh, Xiamen (CN); Rongbin Ling, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 394 days.

(21) Appl. No.: 18/354,136

(22) Filed: Jul. 18, 2023

(65) Prior Publication Data

US 2025/0009729 A1 Jan. 9, 2025

(30) Foreign Application Priority Data

Jul. 7, 2023 (CN) ........................ 202310829734.X

(51) Int. Cl.

| | |
|---|---|
| ***A61K 31/445*** | (2006.01) |
| ***A61K 9/00*** | (2006.01) |
| ***A61K 47/02*** | (2006.01) |
| ***A61K 47/10*** | (2017.01) |
| ***A61K 47/18*** | (2017.01) |
| ***A61K 47/20*** | (2006.01) |
| ***A61K 47/26*** | (2006.01) |
| ***A61K 47/32*** | (2006.01) |
| ***A61K 47/38*** | (2006.01) |

(52) U.S. Cl.

CPC ............ *A61K 31/445* (2013.01); *A61K 9/006* (2013.01); *A61K 47/02* (2013.01); *A61K 47/10* (2013.01); *A61K 47/183* (2013.01); *A61K 47/20* (2013.01); *A61K 47/26* (2013.01); *A61K 47/32* (2013.01); *A61K 47/38* (2013.01)

(58) Field of Classification Search

None

See application file for complete search history.

(56) References Cited

FOREIGN PATENT DOCUMENTS

| | | |
|---|---|---|
| CN | 101511337 | * 8/2009 |
| CN | 108078962 | * 5/2018 |
| CN | 111728958 | * 10/2020 |

* cited by examiner

*Primary Examiner* — Melissa S Mercier

(74) *Attorney, Agent, or Firm* — PERKINS COIE LLP; Viola T. Kung

(57) ABSTRACT

The present invention provides an oral dispersible film for donepezil hydrochloride. The film is a bilayer structure containing a drug layer containing 45-75% w/w donepezil hydrochloride and a backing layer without donepezil hydrochloride. The present oral film retains donepezil hydrochloride in a crystal form and minimizes impurity generation. The oral film contains a selected hydrophobic material to improve the drug stability and minimize the drug solubility.

14 Claims, No Drawings

DONEPEZIL ORAL FILMS

This application claims the priority of Chinese Application No. 202310829734.X, filed Jul. 7, 2023; which is incorporated herein by reference in its entirety.

FIELD OF INVENTION

The present invention provides a bilayer oral film for delivering donepezil hydrochloride in the oral cavity. The bilayer oral film is a stable film and masks an unpleasant taste of drug.

BACKGROUND OF THE INVENTION

Donepezil hydrochloride, chemical name 1-benzyl-4-((5, 6-dimethoxy-1-indanon)-2-yl)methylpiperidine hydrochloride, sold under the brand name Aricept among others, is used in treating a variety of disorders, including dementia and attention deficit disorder. In particular, donepezil hydrochloride is used as a pharmaceutically active agent for treating dementia of the Alzheimer's type. Efficacy has been demonstrated in patients with mild, moderate, and severe Alzheimer's disease.

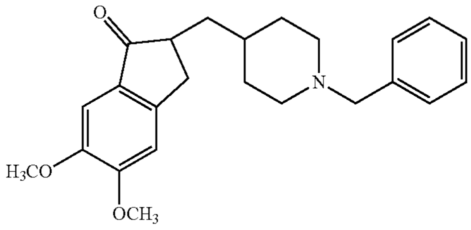

Donepezil

There are various types of dosage formulations of donepezil hydrochloride available for oral administration. Within those preparations, tablets and capsules are widely available but they are disadvantageous for patients having difficulties in taking tablets and capsules. Liquid formulations are disadvantageous due to instability and inaccurate dispensing.

Several formulations with different drug delivery systems are available in the market. ODT (orally dispersible tablet) is one of those formulations. However, the problems are that ODT generally does not completely or consistently disintegrated in a short time due to smaller surface area and thus it frequently requires water after dose. ODTs are fragile and can break during transport. Geriatric and pediatric patients have difficulty chewing or swallowing solid dosage forms. Therefore, many children and elderly people are reluctant to take these solid dosage forms due to fear of asphyxiation.

Psychiatric patients may refuse medication or develop behaviors such as failure to swallow pills and/or expulsion of pills.

There exists a need for a new donepezil hydrochloride formulation in which the drug is stable under common storage conditions, and the formulation provides an acceptable taste in the oral cavity.

DETAILED DESCRIPTION OF THE INVENTION

Definitions

"An oral film", as used herein, refers to a film or strip used in a drug delivery system to deliver a drug. When an oral film is placed in the mouth or on the tongue, it disintegrates or dissolves by the saliva within a few seconds to deliver its content.

"A pharmaceutically acceptable salt," as used herein, is a salt that retains the desired biological activity of the parent compound and does not impart undesired toxicological effects.

"About" when used in this application, refers to +10% of the recited value.

"Donepezil oral film" or "oral donepezil film", as used herein, refers to an oral film comprising an active ingredient donepezil, or a pharmaceutical acceptable salt thereof such as hydrochloride.

Unless otherwise specified, % used in this application refers to weight by weight %.

The inventors have discovered an oral film suitable for oral delivery of donepezil with similar therapeutic efficacy to that of the presently available reference listed drug (RLD) ARICEPT® tablet. The donepezil oral film of the present invention is essentially uniform in thickness, color, and without bubbles. The active ingredient donepezil in the present oral film is in an anhydrous crystalline form which has a slow dissolution rate in the oral cavity, and thus reducing the bitterness produced by the dissolved drug.

The present application provides a pharmaceutical composition comprising donepezil or a pharmaceutical acceptable salt thereof in an oral film, which is rapidly dispersible and is suitable for oral administration of donepezil or a pharmaceutical acceptable salt thereof such as donepezil hydrochloride.

Oral dispersible films have many advantages over other solid dosage forms, including a better flexibility of the film, and increased efficacy of an active principal ingredient (API). Due to the large surface area, oral films can be dissolved and disintegrated with a small amount of saliva. The oral dispersible film is useful for the patients who are bedridden, active working, or traveling. Oral dispersible films offer advantages for treating geriatric patients, pediatric patients, and patients with psychiatric disorders.

The donepezil hydrochloride oral film of the present invention is stable under common storage conditions. The film provides a good taste, and it is essentially uniform in thickness, color, and without bubbles. The donepezil oral film of the present invention makes it acceptable to administer the active ingredient by an oral route.

The present invention provides a bilayer oral donepezil film comprising a drug layer and a backing layer. The drug layer comprises about 45-75% w/w of donepezil, or a pharmaceutically acceptable salt thereof, in a crystalline form, about 5-30% w/w of a first film-forming material, about 2-10% w/w of a first plasticizer, and about 1-15% of one or more first hydrophobic materials. The backing layer comprises 60-95% w/w of a second film-forming material, 1.5-9% w/w of a second plasticizer, 2-10% w/w of one or more second hydrophobic materials.

The active ingredient in the pharmaceutical composition is donepezil or a pharmaceutically acceptable salt thereof, e.g., donepezil hydrochloride. The amount of donepezil or donepezil salt in the present oral film in general is 3-15 mg. The weight percentage of donepezil or donepezil salt in the drug layer is 45-75%, or 45-70%, or 50-75%, or 50-70%, or 60-75% w/w.

The concentration of drug in the drug layer determines the stability of the product. In general, lower donepezil concentration in the drug layer leads to drug dissolution and instability. In the present bilayer form, the donepezil concentration in the drug layer is in a high concentration of at least 45%. Due to the high concentration in the drug layer, most of donepezil remains in a crystal form and maintains the stability.

In a typical oral film, a major component is one or more film-forming materials (often more than 70%), which contribute to the formation and the strength of the film. However, the drug layer of the oral film of the present invention has higher contents of drug than film-forming materials, and therefore, a single drug layer of the film would be brittle, and easily breakable by folding 2-3 times. To resolve this issue, the oral film of the present invention adds a backing layer to the drug layer, which gives the film with acceptable film properties such as appearance, folding endurance, elongation rate, disintegration time, tensile strength, and breaking strength. The backing layer is water-soluble and comprises 60-95%, preferably 70-90% w/w of a second film-forming material to provide the film strength.

Pharmaceutically acceptable film-forming materials are independently used in the drug layer and in backing layer. The pharmaceutically acceptable film-forming materials include hypromellose (HPMC), hydroxypropyl cellulose (HPC), hydroxyethylcellulose (HEC), carboxymethylcellulose sodium (CMC-Na), carboxymethylcellulose calcium (CMC-Ca), carboxymethylcellulose potassium (CMC-K), carboxymethylcellulose (CMC), methylcellulose, polyvinyl ethanol (PVA), copovidone, povidone, ethylene glycol and vinyl ethanol graft copolymer, xanthan gum, pectin, polyethylene oxide (PEO), and chitosan. Preferred film-forming materials include low viscosity materials such as HPMC, HPC, PVA, copovidone, ethylene glycol and vinyl ethanol graft copolymer (PVA-PEG). The preferred viscosity of HPC is from about 100 to 600 mPa·s (millipascal·second) at 10% w/w concentration. The preferred viscosity of HPMC is about 3-100 mPa·s at 2% w/w concentration. The weight percentage of film-forming materials in a drug layer is in general about 5-30% w/w; preferably 10-25% w/w. The weight percentage of film-forming materials in a backing layer is about 60-95% w/w; preferably about 70-90% w/w. The film-forming materials are compatible to donepezil hydrochloride and provide a suitable drug loading capacity, and are able to maintain donepezil hydrochloride in a preferred crystalline form in the drug layer.

In one embodiment, the first and second film-forming materials are independently selected from the group consisting of: HPMC, HPC, xanthan gum, chitosan, carboxymethylcellulose, sodium alginate, copovidone, PVP, or any combination thereof.

In one embodiment, the first and second film-forming materials independently comprise HPMC, HPC, PVP, or a combination thereof. For example, the first film-forming material is HPMC or HPC. For example, the second film-forming material is a combination of HPC and PVP.

One or more hydrophobic materials are used in the drug layer and in the backing layer to improve the stability of the film. Pharmaceutically acceptable hydrophobic materials include magnesium aluminum silicate, titanium dioxide, glyceryl behenate, calcium stearate, stearic acid, hydrogenated vegetable oil, and colloidal silicon dioxide. The hydrophobic material protects the film from moisture absorption. The amount of hydrophobic material in the drug layer is about 1-15%, 2-15%, or 2-12% w/w, preferably 1-10% 2-10% or 2-5% w/w. The amount of hydrophobic material in the backing layer is 1-15%, 2-15%, or 2-12% w/w, preferably 1-10%, 2-10% or 2-5% w/w.

The inventors have demonstrated that the use of a selected hydrophobic material such as titanium dioxide or magnesium aluminum silicate in a drug layer and in a backing layer improves the stability of the drug product. Magnesium aluminum silicate and titanium dioxide are hydrophobic excipients practically insoluble in water and ethanol. The presence of titanium dioxide or magnesium aluminum silicate in the drug layer and in the backing layer reduces the solubility of donepezil hydrochloride and provides a moisture-protective covering to the film, and thus improving the stability of the film. When the drug layer and the back layer does not contain an added hydrophobic material, or contains an undesirable hydrophobic material such as talc or magnesium stearate, the film does not pass the stability test in accelerated stability condition at 40° C. at 75% room humidity for 6 months.

In addition to the above-mentioned components, the drug layer and backing layer of the film also independently contains one or more plasticizers to improve the folding endurance of film and manufacturing processability. A suitable plasticizer includes polyethylene glycol, glycerin, sorbitol or triethyl citrate. A suitable amount of the plasticizer in the drug layer is about 2%-15% w/w, preferably 2-10% w/w. A suitable amount in the backing layer is 2-15% w/w, more preferably 1.5-9% (w/w).

Donepezil, or a pharmaceutically acceptable salt thereof, is bitter in taste, which results in a discomfort feeling in mouth when administered orally. The oral dispersible film of the present invention is in a bilayer film; both layers optionally contain one or more sweetening agents and flavoring agents. Donepezil, or a pharmaceutically acceptable salt, is blended with the sweetening agent and the flavoring agent in the presence of one or more film-forming materials to mask the bitter taste, and thus improving the compliance of a patient.

In one embodiment, one or more sweeteners and one or more flavoring agent are added in the drug layer and/or in the backing layer to mask the bitter taste of donepezil hydrochloride. Examples of sweeteners include sucralose, sucrose, glucose, sodium saccharin, fructose, xylitol, stevia, aspartame, neotame, acesulfame potassium, starch syrup, maltitol, erythritol, xylitol, sorbitol, mannitol, and trehalose. Examples of flavoring agents include menthol, peppermint oil, orange flavor, pineapple flavor, cherry flavor, apple flavor, banana flavor, blueberry flavor, peach flavor, mango flavor, and grape flavor. Sucralose and aspartame are preferred sweeteners. Menthol is a preferred flavoring agent. The amounts of a sweetener in the drug layer and in the backing layer are independently about 2-20% w/w, preferably about 2-10% w/w. The amount of one or more flavoring agents in the drug layer is about 0.5-10% w/w, preferably 0.5-5% (w/w). The amount of one or more flavoring agents in the backing layer about 0.5-10% w/w, preferably 0.5-4% (w/w).

Colors are used to improve the appearance of the film. One or more colors such as FD&C colors, D&C colors, red ferric oxide, yellow ferric oxide, an edible dye may be added into the drug layer and/or the backing layer.

The bilayer oral dispersible film of the present invention masks an unpleasant bitter taste of donepezil hydrochloride by keeping donepezil hydrochloride in a crystal form and optionally adding one or more sweeteners and one or more flavoring agent in the film. The bilayer film provides a good appearance, good film properties, bitter masking, and it retains a crystal form. In the bilayer, the drug layer stabilizes the crystal form and reduces impurity generation due to the high concentration of the drug in the drug layer. The backing layer provides acceptable film properties. Both layers contribute to masking the bitter taste of the drug.

The present invention further provides a method for preparing a donepezil oral dispersible bilayer film. The method comprises the steps of: (a) mixing the second film-forming material, a second hydrophobic material, and a second plasticizer in a first solvent to prepare a backing layer suspension; (b) coating the backing layer suspension on a substrate and drying the suspension to form a backing layer film; (c) mixing donepezil, or a pharmaceutically acceptable salt, a first film-forming material, a first hydrophobic material, and a first plasticizer in a second solvent to form a drug suspension; (d) coating the drug suspension on the backing layer film and drying the drug suspension to form a bilayer film on the substrate, wherein the bilayer film comprises a drug layer film and the backing layer film; and (e) removing the bilayer film from the substrate to form a bilayer donepezil oral film.

During the manufacturing process, donepezil, or a pharmaceutically acceptable salt, is prepared in a suspension form in a suitable solvent, and then the suspension is coated on a substrate and dried to form a film. Drug layer contains donepezil hydrochloride in an anhydrous crystal form III, which is characterized by P-XRD pattern having peaks expressed as 2-theta at about 6.6±0.2, 15.0±0.2, 16.5±0.2, 18.1±0.2, 18.5±0.2, 20.1±0.2, 21.7±0.2, 26.0±0.2 and 28.2±0.2 degrees. The present process selects a suitable solvent to provide a suitable solubility of donepezil, and reduces recrystallization and form conversion of donepezil crystal.

When purified water is used as a solvent, donepezil or a pharmaceutically acceptable salt, is soluble and then it is converted to an amorphous form and retains the amorphous form in the manufactured film. Such film is not stable and the impurities increase during stability study. Further, the amorphous form will convert to a crystalline form during storage to change the physical appearance of the film, resulting to patches on the film.

In steps (a) and (c), to maintain the more stable crystal form of donepezil or a pharmaceutically acceptable salt in the film, the inventors select the combination of water and an organic solvent such as ethanol or methanol to prepare a drug layer suspension and a backing layer suspension. The selected solvents allow all the materials to disperse or dissolve completely and form a homogeneous suspension. In one embodiment, 70 to 95% w/w ethanol or methanol is used as a solvent to prepare for the drug layer film. In one embodiment, 30-70% w/w ethanol or methanol, or 30-60% w/w ethanol is used as a solvent to prepare the backing layer film.

In steps (a) and (c), a sweetening agent, a flavoring agent, and/or a colorant is optionally added in the solvent to prepare each suspension.

In steps (b) and (d), the drying temperature is about 40°-100° C., preferably about 50-80° C.

Substrates suitable for the process include polyethylene terephthalate, polypropylene resins, and polymethylpentene resins.

After step (e), the bilayer film is optionally cut into a suitable size and shape, and then further wrapped or packaged. The donepezil oral dispersible film of the present invention has a length of about 1-4 cm, and a width about 1-4 cm; preferably a length of about 1-3 cm, and width about 1-3 cm.

The use of one or more hydrophobic materials in the drug layer and in the backing layer and the use of a proper solvent in the process of manufacturing the film ensure that donepezil or a pharmaceutically acceptable salt, undergoes negligible solubilization and keeps donepezil or a pharmaceutically acceptable salt in the crystalline state in the drug layer; which brings a better stability of the film. Further, the dissolution rate of donepezil in the crystalline form is slower than that of amorphous form. Amorphous form of donepezil immediately dissolves in the oral cavity of a patient and the patient feels bitterness immediately before swallowing saliva. Crystalline form of donepezil dissolves slowly in the buccal cavity of a patient, which allows time for the patient to swallow saliva and thus the patient feels less bitterness.

The present invention provides a method for treating dementia by orally administering a donepezil oral film to a subject in need thereof. The donepezil oral film is easy to use with a rapid onset of action to significantly improve mental function such as memory, attention, the ability to interact with others, speak, think clearly, and perform regular daily activities. Donepezil may improve the ability to think and remember or slow the loss of these abilities in patients with Alzheimer's disease.

The oral film of the present invention is administered orally by placing the pharmaceutical dosage on top of the tongue in the mouth of a subject. The film adheres to the tongue and dissolves. When the film dissolves, saliva is swallowed in a normal manner, and donepezil, or a pharmaceutically acceptable salt, is absorbed through gastrointestinal track. The absorption of donepezil, or a pharmaceutically acceptable salt, in the present invention is not affected by food, so it can be taken without regard to meals.

The oral dispersible film of the present invention can be orally taken by a patient without water, due to its large surface area in contact with tongue. The oral film can also be taken by a person who is difficult to swallow, such as an elderly person or a person who is bedridden. The oral film has excellent portability and is convenient to be carried by active working people or traveling people.

The following examples further illustrate the present invention. These examples are intended merely to be illustrative of the present invention and are not to be construed as being limiting.

EXAMPLES

Examples 1-6. Donepezil Oral Single Layer Film

The formulation of donepezil hydrochloride oral dispersible film of Examples 1-5 is shown below.

| | |
|---|---|
| Donepezil hydrochloride (crystalline) | 10.00 mg (32.26% w/w) |
| Hypromellose | 16.46 mg (53.10% w/w) |
| PVP | 3.2 mg (10.32% w/w) |
| Aspartame | 1.28 mg (4.13% w/w) |
| FD&C Yellow No. 6 | 0.064 mg (0.21% w/w) |
| Solvent | 120 mg (Removed during drying process) |

Manufacturing Process:

Dissolve/disperse the donepezil hydrochloride into solvent with continuous stirring, add other excipients and continue stirring until the homogenous mixture forms, apply vacuum to remove air bubbles, Coat the defoamed film solution evenly on a substrate, Dry the coating at temperature of about 50° C. to 80° C. to form a film on the conveyor belt, After the film was formed, cut the film into a suitable size, shape and packed in to pouch or in a suitable container.

Examples 1. Single Layer, Water Solvent

In example 1, purified water was used as the solvent. The appearance of the donepezil hydrochloride film was satisfactory. The film could be easily peeled off from the substrate. The film had a smooth appearance and uniform in color. The x-ray powder diffraction shows that the donepezil hydrochloride was in amorphous state in the firm.

Dissolution test was performed in 0.1N HCl using USP I basket apparatus, 50 rpm basket speed, 900 ml media volume. The % release at different time points is shown in Table 1. The dissolution of the film was rapid, more than 85% dissolved in 15 min.

TABLE 1

| Dissolution Test Result | | | | | |
|---|---|---|---|---|---|
| Media | 0.1N HCl | | | | |
| Time (min) | 5 | 10 | 15 | 20 | 30 |
| Dissolved (%) | 65 | 87 | 93 | 97 | 99 |

TABLE 2

Stability data in accelerated stability condition (40° C./75% RH)

| | Related Substances (%) | | | | | | | |
|---|---|---|---|---|---|---|---|---|
| Time (months) | Impurity b | Impurity c | Impurity g | Impurity h | Highest unknown individual impurity | Total impurities | Dissolution (%) | Assay (%) |
| Acceptance criteria | ≤0.15 | ≤0.15 | ≤0.50 | ≤0.50 | ≤0.20 | ≤1.00 | ≥80 in 30 min | 95-105 |
| 0 | 0.07 | NA | 0.09 | 0.05 | 0.03 | 0.24 | 98 | 100.7 |
| 1 | 0.09 | NA | 0.19 | 0.09 | 0.08 | 0.58 | 103 | 102.8 |
| 3 | 0.15 | 0.09 | 0.36 | 0.19 | 0.13 | 1.3 | 100 | 94.5 |
| 6 | 0.20 | 0.11 | 0.61 | 0.74 | 0.39 | 2.8 | 96 | 91.6 |

The accelerated stability data at 40° C./75% RH show that the product was unstable with total impurity level of 2.8% at 6 months (<1.0% is the acceptable limit). During preparation, it was observed that the drug was completely dissolved in the water and converted to an amorphous form. The results show that the amorphous form of donepezil is unstable.

Example 2-5. Single Layer, Different Solvents for Preparation

Examples 2-5 used different solvents or solvent mixtures to prepare the donepezil film. The formulation details of the trial are as follows,

| Example No. | 2 | 3 | 4 | 5 |
|---|---|---|---|---|
| Donepezil hydrochloride | 10.00 mg (31.25% w/w) | 10.00 mg (31.25% w/w) | 10.00 mg (31.25% w/w) | 10.00 mg (31.25% w/w) |
| hydroxypropyl cellulose | 15.86 mg (49.56% w/w) | 15.86 mg (49.56% w/w) | 15.86 mg (49.56% w/w) | 15.86 mg (49.56% w/w) |
| copovidone | 3.2 mg (10% w/w) | 3.2 mg (10% w/w) | 3.2 mg (10% w/w) | 3.2 mg (10% w/w) |
| PEG 400 | 1.6 mg (5% w/w) | 1.6 mg (5% w/w) | 1.6 mg (5% w/w) | 1.6 mg (5% w/w) |
| Aspartame | 1.28 mg (4% w/w) | 1.28 mg (4% w/w) | 1.28 mg (4% w/w) | 1.28 mg (4% w/w) |
| FD&C Yellow No. 6 | 0.064 mg (0.2% w/w) | 0.064 mg (0.2% w/w) | 0.064 mg (0.2% w/w) | 0.064 mg (0.2% w/w) |
| 40% Ethanol | 130 mg | — | — | — |
| Isopropanol | — | 125 mg | — | — |
| 80% Isopropanol | — | — | 125 mg | — |
| Acetone | — | — | — | 120 mg |

Note:
The solvents used in the manufacturing were removed during the process of drying.

The donepezil hydrochloride oral dispersible film prepared with 40% Ethanol (example 2) had smooth appearance and uniform in color and was better than the other batches. In summary, in Examples 1 and 2, the drug was completely dissolved and converted to amorphous this leads to increase in impurities.

The films prepared with isopropanol and acetone (example 3 and 5 respectively) were not uniform in appearance and was easily detached from the base substrate, and it was difficult to perform the cutting and packing process.

An x-ray powder diffraction test was conducted on the film prepared with 40% ethanol in Example 2. On day 0, the film was in an amorphous form, but it changed to a crystalline form, and patches were seen on the surface of the film after 30 days in 40° C./75% RH condition.

The dissolution of the film prepared with 40% ethanol was rapid as more than 85% was dissolved in 15 min.

Donepezil hydrochloride in an amorphous form rapidly dissolves in the oral cavity, which results in a very bitter taste and is not desirable.

Example 6. Single Layer, 70% Ethanol for Preparation

In this experiment, the donepezil hydrochloride oral dispersible film was prepared using 70% ethanol. The formulation is shown below.

| | |
|---|---|
| Donepezil hydrochloride | 10.00 mg (31.25% w/w) |
| Hypromellose | 16.14 mg (50.44% w/w) |
| PEG 400 | 3.2 mg (10% w/w) |
| Aspartame | 1.6 mg (5% w/w) |
| Titanium dioxide | 1.00 mg (3.13% w/w) |
| FD&C Yellow No. 6 | 0.064 mg (0.2% w/w) |
| 70% ethanol | 130 mg |

Note:
The solvents used in the manufacturing process removed during the process of drying.

The donepezil hydrochloride oral dispersible film prepared with 70% ethanol had smooth appearance and was uniform in color. The stability results showed that total impurities were acceptable (0.73%) at 3 months, but not acceptable at (1.12%) at 6 months. (Table 3)

TABLE 3

| Stability data in accelerated stability condition (40° C./75% RH) | | | | | | | | |
|---|---|---|---|---|---|---|---|---|
| | Related Substances (%) | | | | | | | |
| Time (months) | Impurity b | Impurity c | Impurity g | Impurity h | Highest unknown individual impurity | Total impurities | Dissolution (%) | Assay (%) |
| Acceptance criteria | ≤0.15 | ≤0.15 | ≤0.50 | ≤0.50 | ≤0.20 | ≤1.00 | ≥80 in 30 min | 95-105 |
| 0 | 0.003 | 0.001 | 0.09 | 0.004 | 0.08 | 0.17 | 98 | 100.03 |
| 1 | 0.07 | 0.06 | 0.09 | 0.018 | 0.09 | 0.40 | 99 | 100.11 |
| 3 | 0.13 | 0.10 | 0.15 | 0.15 | 0.14 | 0.73 | 96 | 99.03 |
| 6 | 0.15 | 0.13 | 0.18 | 0.23 | 0.18 | 1.12* | 94 | 98.21 |

*not acceptable

Example 7-9. Bilayer Films

In Examples 7-9, the donepezil hydrochloride oral dispersible films were in a bilayer form. The drug layers of Examples 7-9 were the same, and were prepared according to Example 1. The backing layers of Example 7-9 were prepared using different concentrations of ethanol or water. The backing layer was coated on the substrate first, and then a drug layer was coated on the backing layer. The formulation details are shown below.

| | Example | 7 | 8 | 9 |
|---|---|---|---|---|
| DL[1] | Donepezil hydrochloride | 10.00 mg (62.94% w/w) | 10.00 mg (62.94% w/w) | 10.00 mg (62.94% w/w) |
| | Hydroxypropyl cellulose | 3.00 mg (18.88% w/w) | 3.00 mg (18.88% w/w) | 3.00 mg (18.88% w/w) |
| | PEG 400 | 1.1 mg (6.92% w/w) | 1.1 mg (6.92% w/w) | 1.1 mg (6.92% w/w) |
| | Aspartame | 0.42 mg (2.64% w/w) | 0.42 mg (2.64% w/w) | 0.42 mg (2.64% w/w) |
| | Titanium dioxide | 1.35 mg (8.50% w/w) | 1.35 mg (8.50% w/w) | 1.35 mg (8.50% w/w) |
| | FD&C Yellow No. 6 | 0.018 mg (0.11% w/w) | 0.018 mg (0.11% w/w) | 0.018 mg (0.11% w/w) |
| | 70% ethanol | 50.00 mg | 50.00 mg | 50.00 mg |
| BL[2] | Hypromellose | 10.0 mg (62.07% w/w) | 10.0 mg (62.07% w/w) | 10.0 mg (62.07% w/w) |
| | PVP | 3.53 mg (21.91% w/w) | 3.53 mg (21.91% w/w) | 3.53 mg (21.91% w/w) |

-continued

| Example | 7 | 8 | 9 |
|---|---|---|---|
| PEG 400 | 0.45 mg (2.79% w/w) | 0.45 mg (2.79% w/w) | 0.45 mg (2.79% w/w) |
| Aspartame | 0.80 mg (4.97% w/w) | 0.80 mg (4.97% w/w) | 0.80 mg (4.97% w/w) |
| Titanium dioxide | 1.30 mg (8.07% w/w) | 1.30 mg (8.07% w/w) | 1.30 mg (8.07% w/w) |
| FD&C Yellow No. 6 | 0.03 mg (0.19% w/w) | 0.03 mg (0.19% w/w) | 0.03 mg (0.19% w/w) |
| 70% ethanol | 65 mg | — | — |
| 40% ethanol | — | 70 mg | — |
| Water | — | — | 70 mg |

[1]DL refers to Drug Layer;
[2]BL refers to Backing Layer.
Note:
The solvents used in the manufacturing process removed during the process of drying.

The donepezil hydrochloride oral dispersible films of all the batches (Examples 7-9) were smooth and uniform in color. The XRD result of Example 8 shows that donepezil hydrochloride was in crystal form at Day 0 and retained the same crystal form after 90 days of stability study. The results show that 70% ethanol is suitable for preparing a drug layer and maintaining the crystalline form. The results also showed that 40-70% ethanol are suitable for preparing backing layer.

The dissolution of the film was rapid and 95% was dissolved in 15 min.

TABLE 4

| Stability data in accelerated stability condition (40° C./75% RH) - Example 8 | | | | | | | | |
|---|---|---|---|---|---|---|---|---|
| | Related Substances (%) | | | | | | | |
| Time (months) | Impurity b | Impurity c | Impurity g | Impurity h | Highest individual impurity | Total impurities | Dissolution at 30 min (%) | Assay (%) |
| Acceptance criteria | ≤0.15 | ≤0.15 | ≤0.50 | ≤0.50 | ≤0.20 | ≤1.00 | ≥80 in 30 min | 95-105 |
| 0 | 0.001 | NA | 0.02 | 0.001 | 0.01 | 0.04 | 95 | 99.98 |
| 1 | 0.04 | NA | 0.03 | 0.009 | 0.02 | 0.15 | 100 | 100.13 |
| 3 | 0.06 | 0.03 | 0.05 | 0.012 | 0.05 | 0.23 | 99 | 98.89 |
| 6 | 0.09 | 0.07 | 0.08 | 0.013 | 0.06 | 0.33 | 101 | 99.01 |

The stability results of Example 8 show that the film was stable in accelerated condition (40° C./75% RH) for 6 months. The appearance of the film was good but the film was little bitter in taste.

In summary, in Example 8 (bilayer), the drug retained crystal form and the product is stable after 6 months, which is better than the stability of Example 6 (single layer).

The results of XRD graphs of Examples 6 and 8 show that the intensities of peaks of Example 8 are sharper and better than those of Example 6, which suggest that there might be some dissolution of drug in Example 6.

Examples 10-13. Bilayer Film, Different Hydrophobic Materials

In Examples 10-13, the donepezil hydrochloride oral dispersible films were prepared in a bilayer form, using magnesium stearate, talc, and magnesium aluminum silicate as a hydrophobic material to replace titanium dioxide in the formulation. The formulation details are as below.

The drug layer and backing layer suspension prepared separately, the preparation method is same as in example 1. A backing layer was first coated on the substrate, and then a drug layer was coated on the backing layer. The film of Example 12 (talc) was easily detached from the base substrate, which made it was difficult to perform the cutting and packaging process.

| | Example | 10 | 11 | 12 | 13 |
|---|---|---|---|---|---|
| DL[1] | Donepezil hydrochloride | 10.0 mg (62.93% w/w) | 10.0 mg (62.93% w/w) | 10.0 mg (62.93% w/w) | 10.0 mg (62.93% w/w) |
| | Hypromellose | 3.9 mg (24.55% w/w) | 3.00 mg (18.88% w/w) | 3.00 mg (18.88% w/w) | 3.55 mg (22.34% w/w) |
| | PEG 400 | 1.32 mg (8.31% w/w) | 1.1 mg (6.92% w/w) | 1.1 mg (6.92% w/w) | 1.1 mg (6.92% w/w) |
| | Aspartame | 0.65 mg (4.09% w/w) | 0.42 mg (2.64% w/w) | 0.42 mg (2.64% w/w) | 0.42 mg (2.64% w/w) |
| | Magnesium stearate | — | 1.35 mg (8.50% w/w) | — | — |
| | Talc | — | — | 1.35 mg (8.50% w/w | — |
| | Magnesium Aluminum Silicate | — | — | — | 0.80 mg (5.03% w/w) |
| | FD&C Yellow No. 6 | 0.018 mg (0.11% w/w) | 0.018 mg (0.11% w/w) | 0.018 mg (0.11% w/w) | 0.018 mg (0.11% w/w) |
| | 70% ethanol | 50.00 mg | 50.00 mg | 50.00 mg | 50.00 mg |
| BL[2] | Hypromellose | 10.00 mg (62.07% w/w) | 10.00 mg (62.07% w/w) | 10.00 mg (62.07% w/w) | 10.5 mg (65.18%w/w) |
| | PVP | 4.83 mg (29.98% w/w) | 3.53 mg (21.91% w/w) | 3.53 mg (21.91% w/w) | 3.53 mg (21.91% w/w) |
| | PEG 400 | 0.45 mg (2.79% w/w) | 0.45 mg (2.79% w/w) | 0.45 mg (2.79% w/w) | 0.45 mg (2.79% w/w) |
| | Aspartame | 0.8 mg (4.97% w/w) | 0.8 mg (4.97% w/w) | 0.8 mg (4.97% w/w) | 0.8 mg (4.97% w/w) |
| | Magnesium stearate | — | 1.3 mg (8.07% w/w) | — | — |
| | Talc | — | — | 1.3 mg (8.07% w/w) | — |
| | Magnesium Aluminum Silicate | — | — | — | 0.80 mg (4.97%w/w) |
| | FD&C Yellow No. 6 | 0.03 mg (0.19% w/w) | 0.03 mg (0.19% w/w) | 0.03 mg (0.19% w/w) | 0.03 mg (0.19% w/w) |
| | 40% Ethanol | 70 mg | 70 mg | 70 mg | 70 mg |

[1]DL refers to Drug Layer;
[2]BL refers to Backing Layer.
Note:
The solvents used in the manufacturing process removed during the process of drying.

TABLE 5

Stability data in accelerated stability condition (40° C./75% RH) - Example 10 (no added hydrophilic material)

| Time (months) | Related Substances (%) Impurity b | Impurity c | Impurity g | Impurity h | Highest individual impurity | Total impurities | Dissolution at 30 min (%) | Assay (%) |
|---|---|---|---|---|---|---|---|---|
| Acceptance criteria | ≤0.15 | ≤0.15 | ≤0.50 | ≤0.50 | ≤0.20 | ≤1.00 | ≥80 in 30 min | 95-105 |
| 0 | 0.001 | NA | 0.01 | 0.003 | 0.01 | 0.09 | 98 | 100.03 |
| 1 | 0.06 | 0.05 | 0.06 | 0.012 | 0.06 | 0.28 | 99 | 100.11 |
| 3 | 0.10 | 0.07 | 0.11 | 0.11 | 0.12 | 0.68 | 96 | 99.03 |
| 6 | 0.17* | 0.1 | 0.15 | 0.20 | 0.15 | 0.88 | 94 | 98.21 |

*not acceptable

TABLE 6

Stability data in accelerated stability condition (40° C./75% RH) - Example 11 (magnesium stearate)

| Time (months) | Related Substances (%) Impurity b | Impurity c | Impurity g | Impurity h | Highest individual impurity | Total impurities | Dissolution at 30 min (%) | Assay (%) |
|---|---|---|---|---|---|---|---|---|
| Acceptance criteria | ≤0.15 | ≤0.15 | ≤0.50 | ≤0.50 | ≤0.20 | ≤1.00 | ≥80 in 30 min | 95-105 |
| 0 | 0.002 | NA | 0.009 | 0.008 | 0.01 | 0.07 | 100 | 100.15 |
| 1 | 0.08 | 0.05 | 0.09 | 0.014 | 0.06 | 0.32 | 98 | 99.52 |
| 3 | 0.11 | 0.06 | 0.15 | 0.17 | 0.11 | 0.74 | 97 | 99.01 |
| 6 | 0.14 | 0.09 | 0.19 | 0.23 | 0.17 | 1.11* | 94 | 97.51 |

*not acceptable

TABLE 7

Stability data in accelerated stability condition (40° C./75% RH) - Example 13 (magnesium aluminum silicate)

| Time (months) | Related Substances (%) Impurity b | Impurity c | Impurity g | Impurity h | Highest individual impurity | Total impurities | Dissolution at 30 min (%) | Assay (%) |
|---|---|---|---|---|---|---|---|---|
| Acceptance criteria | ≤0.15 | ≤0.15 | ≤0.50 | ≤0.50 | ≤0.20 | ≤1.00 | ≥80 in 30 min | 95-105 |
| 0 | 0.001 | NA | 0.01 | 0.001 | 0.007 | 0.07 | 95 | 99.98 |
| 1 | 0.02 | NA | 0.03 | 0.007 | 0.01 | 0.11 | 100 | 100.13 |
| 3 | 0.05 | 0.01 | 0.05 | 0.011 | 0.03 | 0.17 | 99 | 98.89 |
| 6 | 0.08 | 0.03 | 0.07 | 0.013 | 0.04 | 0.25 | 101 | 99.01 |

The results of Tables 4-7 show that the presence of a hydrophobic material of titanium dioxide or magnesium aluminum silicate improves the stability of the product. Magnesium aluminum silicate (Example 13) and titanium dioxide (Example 8) are hydrophobic excipient practically insoluble in water and ethanol, it is believed that magnesium aluminum silicate or titanium dioxide in the formulation reduces the solubility of donepezil hydrochloride and provides a moisture protective coating, and thus improves the stability of the film.

Bitterness of the films of Example 2, Example 6 and Example 8 were tested in 10 volunteers. Each volunteer was given 3 films one from each batch to place on tongue and record the taste. The feedback of 10 volunteers was recorded. Out of 10, all the volunteers said Example 2 was very bitter and difficult to handle; Example 6 was less bitter than Example 2, but still unacceptable; and Example 8 was better than Examples 2 and 6, but it still needs some improvement.

As discussed earlier, when the film contains donepezil in an amorphous form instead of a crystalline form, amorphous donepezil rapidly dissolves in the oral cavity and a subject feels bitterness before swallowing saliva.

Example 14-15. Bilayer Film, with Sweetener and Flavoring Agent

In these examples, the donepezil hydrochloride oral dispersible films were prepared in a bilayer form, sweetener in different concentration and combination of sweetener and flavoring agent were evaluated. The formulation details are given below.

The bilayer films were prepared according to the methods described before.

| | Example | 14 | 15 |
|---|---|---|---|
| DL[1] | Donepezil hydrochloride | 10.00 mg (62.94% w/w) | 10.00 mg (62.94% w/w) |
| | Hypromellose | 2.77 mg (17.43% w/w) | 3.00 mg (18.88% w/w) |
| | PEG 400 | 1.1 mg (6.92% w/w) | 1.1 mg (6.92% w/w) |
| | Aspartame | 1 mg (6.29% w/w) | 0.42 mg (2.64% w/w) |
| | Menthol | | 0.15 (0.94% w/w) |
| | Titanium dioxide | 1 mg (6.29% w/w) | 1.20 mg (7.55% w/w) |
| | FD&C Yellow No. 6 | 0.018 mg (0.11% w/w) | 0.018 mg (0.11% w/w) |
| | 70% ethanol | 50.00 mg | 50.00 mg |
| BL[2] | Hypromellose | 9.60 (59.59% w/w) | 9.80 (60.83% w/w) |
| | PVP | 3.53 (21.91% w/w) | 3.53 (21.91% w/w) |
| | PEG 400 | 0.45 (2.79% w/w) | 0.45 (2.79% w/w) |
| | Sucralose | 1.2 (7.45% w/w) | 0.8 (4.97% w/w) |
| | Menthol | — | 0.2 (1.24% w/w) |
| | Titanium dioxide | 1.3 (8.07% w/w) | 1.3 (8.07% w/w) |
| | FD&C Yellow No. 6 | 0.03 (0.19% w/w) | 0.03 (0.19% w/w) |
| | Water | 70 mg | 70 mg |

[1]DL refers to Drug Layer;
[2]BL refers to Backing Layer.
Note:
The solvents used in the manufacturing process removed during the process of drying.

10 volunteers were selected to study the palatability of donepezil hydrochloride oral dispersible films of Example 9, Example 14 and Example 15. Each individual was given 3 films one from each batch to place on tongue and the taste was recorded. Out of 10, seven subjects said that Example 15 had better taste than the other two batches.

However, the surface of backing layer of Example 15 was not smooth; granular structures were seen on the film because menthol was insoluble in water.

Examples 16-17. Bilayer Film, Different Concentrations of Ethanol in Backing Layer Donepezil hydrochloride oral dispersible films were prepared in a bilayer form, and different concentrations of ethanol used for preparing the backing layers. The formulation details are given below. The bilayer films were prepared according to the methods described before.

| | Example | 16 | 17 |
|---|---|---|---|
| DL[1] | Donepezil hydrochloride | 10.00 mg (62.94% w/w) | 10.00 mg (62.94% w/w) |
| | Hypromellose | 2.7 mg (16.99% w/w) | 2.7 mg (16.99% w/w) |
| | PEG 400 | 1.4 mg (8.81% w/w) | 1.4 mg (8.81% w/w) |
| | Aspartame | 0.42 mg (2.64% w/w) | 0.42 mg (2.64% w/w) |
| | Menthol | 0.15 (0.94% w/w) | 0.15 (0.94% w/w) |
| | Titanium dioxide | 1.20 mg (7.55% w/w) | 1.20 mg (7.55% w/w) |
| | FD&C Yellow No. 6 | 0.018 mg (0.11% w/w) | 0.018 mg (0.11% w/w) |
| | 70% ethanol | 50.00 mg | 50.00 mg |
| BL[2] | Hypromellose | 7.10 (44.07% w/w) | 7.10 (44.07% w/w) |
| | PVP | 6.23 (38.67% w/w) | 6.23 (38.67% w/w) |
| | PEG 400 | 0.45 (2.79% w/w) | 0.45 (2.79% w/w) |
| | Sucralose | 0.5 (3.10% w/w) | 0.5 (3.10% w/w) |
| | Menthol | 0.2 (1.24% w/w) | 0.2 (1.24% w/w) |
| | Titanium dioxide | 1.6 (9.93% w/w) | 1.6 (9.93% w/w) |
| | FD&C Yellow No. 6 | 0.03 (0.19% w/w) | 0.03 (0.19% w/w) |
| | 30% Ethanol | 70 mg | — |
| | 60% Ethanol | — | 65 mg |

[1]DL refers to Drug Layer;
[2]BL refers to Backing Layer.
Note:
The solvents used in the manufacturing process removed during the process of drying.

Films of both the Examples 16 and 17 showed a good, smooth, and uniform in appearance. Bitterness of donepezil hydrochloride is completely masked. The dissolution of the film was rapid, with more than 85% dissolved in 15 min.

Example 18-19. Bilayer Film, Study Excipient Range

In this example, the donepezil hydrochloride oral dispersible film was prepared in bilayer form with different concentrations of excipients to study the range. The formulation details are given below. The bilayer films were prepared according to the methods described above.

| | Example | 18 | 19 |
|---|---|---|---|
| DL[1] | Donepezil hydrochloride | 7.20 mg (45.00% w/w) | 12.00 mg (75.00% w/w) |
| | Hydroxy propyl cellulose | 4.00 mg (25.00% w/w) | 1.6 mg (10.00% w/w) |
| | PEG 400 | 0.32 mg (2.00% w/w) | 1.6 mg (10.00% w/w) |
| | Aspartame | 1.6 mg (10.00% w/w) | 0.32 mg (2.00% w/w) |
| | Menthol | 0.8 (5.00% w/w) | 0.08 (0.5% w/w) |
| | Titanium dioxide | 1.92 mg (12.00% w/w) | 0.32 mg (2.00% w/w) |
| | FD&C Yellow No. 6 | 0.16 mg (1.00% w/w) | 0.08 mg (0.5% w/w) |
| | 95% ethanol | — | 50.00 mg |
| | 70% ethanol | 50.00 mg | — |
| BL[2] | Hypromellose | 10.40 (65.00% w/w) | 12.80 (80.00% w/w) |
| | PVP | 0.8 (5.00% w/w) | 1.6 (10.00% w/w) |
| | PEG 400 | 1.44 (9.00% w/w) | 0.24 (1.5% w/w) |
| | Sucralose | 1.6 (10.00% w/w) | 0.32 (2.00% w/w) |
| | Menthol | 0.08 (0.5% w/w) | 0.64 (4.00% w/w) |
| | Titanium dioxide | 1.6 (10.00% w/w) | 0.32 (2.00% w/w) |
| | FD&C Yellow No. 6 | 0.08 (0.5% w/w) | 0.08 (0.5% w/w) |
| | 30% Ethanol | 70 mg | 70 mg |

[1]DL refers to Drug Layer;
[2]BL refers to Backing Layer.
Note:
The solvents used in the manufacturing process removed during the process of drying.

Films of both the Examples 18 and 19 showed a good, smooth, and uniform in appearance. The physical parameters of films are satisfactory. The taste of the film is acceptable.

Example 20. Single Layer, Comparison Purpose

In this example, the donepezil hydrochloride oral dispersible film was prepared in single layer form using combination of film former HPC and Hypromellose, The formulation details are given below. The preparation method is same as in example 1.

| Example | 20 |
|---|---|
| Donepezil hydrochloride | 10.00 mg (31.25% w/w) |
| Hypromellose | 10.50 mg (32.81% w/w) |
| HPC | 7.42 mg (23.19% w/w) |
| PEG 400 | 1.1 mg (3.44% w/w) |
| Sucralose | 1.2 mg (3.75% w/w) |
| Menthol | 0.25 (0.78% w/w) |
| Titanium dioxide | 1.50 mg (4.69% w/w) |
| FD&C Yellow No. 6 | 0.03 mg (0.09% w/w) |
| 70% ethanol | 120.00 mg |

Note:
The solvents used in the manufacturing process removed during the process of drying.

The donepezil hydrochloride oral dispersible film of Example 20 is smooth and uniform in color. In dissolution more than 85% drug released in 15 min.

Example 21. Bilayer Film, Sodium Lauryl Sulfate Added

Donepezil hydrochloride oral dispersible film was prepared in a bilayer form, Sodium lauryl sulfate was added in drug layer to check its effect on absorption of donepezil hydrochloride in a bioequivalence study. The formulation details are given below. The bilayer films were prepared according to the methods described before.

The drug layer and backing layer suspension prepared separately, the preparation method is same as in example 1. First backing layer coated on the substrate then drug layer coated on the backing layer.

| | Example | 21 |
|---|---|---|
| DL[1] | Donepezil hydrochloride | 10.00 mg (62.00% w/w) |
| | Hypromellose | 3.00 mg (18.60% w/w) |
| | Sodium Lauryl Sulfate | 0.24 (1.49% w/w) |
| | PEG 400 | 1.1 mg (6.82% w/w) |
| | Aspartame | 0.42 mg (2.60% w/w) |
| | Menthol | 0.15 (0.93% w/w) |
| | Titanium dioxide | 1.20 mg (7.44% w/w) |
| | FD&C Yellow No. 6 | 0.018 mg (0.11% w/w) |
| | 70% ethanol | 50.00 mg |
| BL[2] | Hypromellose | 9.56 (60.24% w/w) |
| | Copovidone | 3.53 (22.24% w/w) |
| | PEG 400 | 0.45 (2.84% w/w) |
| | Sucralose | 0.8 (5.04% w/w) |
| | Menthol | 0.2 (1.26% w/w) |
| | Titanium dioxide | 1.3 (8.19% w/w) |
| | FD&C Yellow No. 6 | 0.03 (0.19% w/w) |
| | 30% Ethanol | 70 mg |

[1]DL refers to Drug Layer;
[2]BL refers to Backing Layer.
Note:
The solvents used in the manufacturing process removed during the process of drying.

The donepezil hydrochloride oral dispersible film of Example 21 is smooth and uniform in color. The drug release in dissolution study was rapid; more than 85% released in 15 minutes.

Example 22. Bioequivalence Study of Donepezil Hydrochloride Oral Dispersible Films Bioequivalence study was performed on films of Example 16, 20 and 21. In this study, 10 mg Donepezil hydrochloride in the oral dispersible film and reference ARICEPT® 10 mg Tablet were tested. The details of the study are as follows, Design: Randomized, open, single dose, two way crossover design Types of study: Fasting and fed Strength: 10 mg Subjects: Males and non-pregnant females, non-lactating females, general population.

A total of 28 healthy subjects were enrolled in each of the study, two studies performed for each example (fast and fed). Subjects were randomly assigned to one of two dosing sequences according to a randomization table. In the first cycle, they were given a single dose of 10 mg reference donepezil hydrochloride ARICEPT® tablets or 10 mg donepezil hydrochloride oral dispersible film (Example 16, 20, or 21) under study conditions. The blood samples were taken before administration (0 min), and 0.25 h, 0.5 h, 1 h, 1.5 h, 2 h, 2.5 h, 3 h, 3.5 h, 4 h, 5 h, 6 h, 8 h, 12 h, 24 h, 36 h, 48 h and 72 h after administration. The blood samples were then used to determine the donepezil hydrochloride plasma concentration via the HPLC-MS/MS method and to calculate the bioavailability of the films prepared in the examples. After a washout period of at least 21 days, the subject enters the second cycle, where they either took donepezil hydrochloride tablets or donepezil hydrochloride oral dispersible films, and performed the same operation according to the time point of the first cycle.

The results are shown in Tables 8-9 below.

TABLE 8

| Bioavailability Test results under fed condition | | | |
|---|---|---|---|
| Pharmacokinetic parameter | Example 16 | Example 20 | Example 21 |
| 90% confidence interval | | | |
| $C_{max}$ (ng/ml) | 89.42%-104.07% | 71.05%-86.59% | 112.23%-132.07% |
| $AUC_{0-t}$ (h * ng/ml) | 100.52%-112.84% | 75.19%-91.33% | 105.16%-123.47% |

TABLE 9

| Bioavailability Test results under fasting condition | | | |
|---|---|---|---|
| Pharmacokinetic parameter | Example 16 | Example 20 | Example 21 |
| 90% confidence interval | | | |
| $C_{max}$ (ng/mL) | 91.93%-105.61% | 73.28%-89.19% | 116.11%-133.97% |
| $AUC_{0-t}$ (h * ng/ml) | 104.78%-109.72% | 77.00%-90.89% | 110.36%-128.53% |

Table 8 and 9 show that the test results: 90% confidence interval of the ratios of main pharmacokinetic parameters Cmax (ng/mL) and AUC0-t (h*ng/ml), for healthy subjects who orally took 10 mg of donepezil hydrochloride oral dispersible films vs. 10 mg of donepezil hydrochloride tablets (ARICEPT®) under fast and fed conditions.

After evaluating the bioequivalence data of all the batches, Example 16 shows a bioequivalent to the reference listed drug as the results were between acceptable limit of 80.00% to 125.00%. Therefore, Example 16 was selected for a third study (administration of films without drinking water). The films of Example 16 were administered to patients in a fasting state without drinking water, whereas reference drug ARICEPT® 10 mg Tablets were given to patients with the water. The study performed same as stated above and results are shown in Table 10.

TABLE 10

| Bioavailability Test results under fasting condition | |
|---|---|
| Pharmacokinetic parameter | Example 16 |
| 90% confidence interval | |
| $C_{max}$ (ng/mL) | 95.03%-110.83% |
| $AUC_{0-t}$ (h * ng/ml) | 107.08%-112.11% |

Table 10 shows that the donepezil hydrochloride oral dispersible films of Example 16 were bioequivalent to reference ARICEPT® tablet in the studied conditions.

The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. An oral donepezil film, comprising:

(a) a drug layer comprising 45-75% w/w of donepezil or a pharmaceutical acceptable salt thereof, in a crystalline form, 5-30% w/w of a first film-forming material, a first plasticizer, and 2-12% w/w of a first hydrophobic material of titanium dioxide or magnesium aluminum silicate; and (b) a backing layer comprising 60-95% w/w of a second film-forming material, a second plasticizer, 2-12% w/w of a second hydrophobic material of titanium dioxide or magnesium aluminum silicate;

wherein the first and second film-forming materials are independently selected from the group consisting of: hypromellose (HPMC), hydroxypropyl cellulose (HPC), xanthan gum, chitosan, carboxymethylcellulose, sodium alginate, copovidone, polyvinylpyrrolidone (PVP), or any combination thereof.

2. The oral film of claim 1, wherein the drug layer comprises 10-25% w/w of the first film-forming material.

3. The oral film of claim 1, wherein the first film-forming material is HPMC or HPC.

4. The oral film of claim 1, wherein the second film-forming material is HPMC, HPC, PVP, or any combination thereof.

5. The oral film of claim 1, wherein the first and the second plasticizer are independently triethyl citrate, glycerin, or polyethylene glycol 400.

6. The oral film of claim 1, wherein the drug layer comprises 2-10% w/w of the first plasticizer, and the backing layer comprises 1.5-9% w/w of the second plasticizer.

7. The oral film of claim 1, wherein the drug layer and the backing layer further comprises a sweetening agent and/or a flavoring agent.

8. The oral film of claim 7, wherein the flavoring agent is menthol.

9. The oral film of claim 1, wherein the drug layer comprises 45-75% w/w of donepezil hydrochloride, 10-25% w/w of HPMC or HPC, 2-10% w/w of triethyl citrate, glycerin, or polyethylene glycol 400, and 2-12% w/w of titanium dioxide or magnesium aluminum silicate, and the backing layer comprises 70-90% w/w of HPMC or HPC, 1.5-9% w/w of triethyl citrate, glycerin, or polyethylene glycol 400, and 2-10% w/w of titanium dioxide or magnesium aluminum silicate.

10. A process for preparing the oral film of claim 1, comprising the steps of:

(a) mixing the second film-forming material, the second hydrophobic material, the second plasticizer in 30-70% w/w ethanol to prepare a backing layer suspension;

(b) coating the backing layer suspension on a substrate and drying the suspension to form a backing layer film;

(c) mixing donepezil hydrochloride, the first film-forming material, the first hydrophobic material, a first plasticizer in 70-95% w/w ethanol to form a drug suspension;

(d) coating the drug suspension on the backing layer film and drying the drug suspension to form a bilayer film on the substrate, wherein the bilayer film comprises a drug layer film and the backing layer film; and (e) removing the bilayer film from the substrate to form a bilayer donepezil hydrochloride oral film.

11. The oral donepezil film of claim 1, wherein the first hydrophobic material and the second hydrophobic material are titanium dioxide.

12. The oral donepezil film of claim 1, wherein the first hydrophobic material and the second hydrophobic material are magnesium aluminum silicate.

13. The oral donepezil film of claim 9, wherein the drug layer comprises 2-12% w/w of titanium dioxide and the backing layer comprises 2-10% w/w of titanium dioxide.

14. The oral donepezil film of claim 9, wherein the drug layer comprises 2-12% w/w of magnesium aluminum silicate and the backing layer comprises 2-10% w/w of magnesium aluminum silicate.

* * * * *